(12) United States Patent
Shimuta et al.

(10) Patent No.: US 9,510,759 B2
(45) Date of Patent: Dec. 6, 2016

(54) PULSE WAVE PROPAGATION TIME MEASUREMENT DEVICE

(71) Applicant: Murata Manufacturing Co., Ltd., Nagaokakyo-shi, Kyoto-fu (JP)

(72) Inventors: Toru Shimuta, Nagaokakyo (JP); Takanori Hayashi, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 14/750,260

(22) Filed: Jun. 25, 2015

(65) Prior Publication Data
US 2015/0366473 A1 Dec. 24, 2015

Related U.S. Application Data

(63) Continuation of application No. PCT/JP2014/051464, filed on Jan. 24, 2014.

(30) Foreign Application Priority Data

Feb. 26, 2013 (JP) .................................. 2013-035546

(51) Int. Cl.
*A61B 5/04* (2006.01)
*A61B 5/021* (2006.01)
(Continued)

(52) U.S. Cl.
CPC ......... *A61B 5/02125* (2013.01); *A61B 5/0245* (2013.01); *A61B 5/02416* (2013.01);
(Continued)

(58) Field of Classification Search
CPC ............ A61B 5/02125; A61B 5/02416; A61B 5/0245; A61B 5/0452; A61B 5/0456; A61B 5/7289
See application file for complete search history.

(56) References Cited

U.S. PATENT DOCUMENTS

| 4,802,486 A | * | 2/1989 | Goodman | .......... A61B 5/02416 600/324 |
|---|---|---|---|---|
| 5,423,325 A | | 6/1995 | Burton | |

(Continued)

FOREIGN PATENT DOCUMENTS

| JP | H04-200439 A | 7/1992 |
|---|---|---|
| JP | H07171119 A | 7/1995 |

(Continued)

OTHER PUBLICATIONS

International Search Report issued for PCT/JP2014/051464, date of mailing Mar. 11, 2014.

(Continued)

*Primary Examiner* — George Manuel
(74) *Attorney, Agent, or Firm* — Arent Fox LLP

(57) ABSTRACT

A pulse wave propagation time measurement device including a first signal processor section that filters an electrocardiographic signal detected by an electrocardiographic sensor, a second signal processor section that filters a photoelectric pulse wave signal detected by a photoelectric pulse wave sensor, peak detectors respectively that detect peaks of the electrocardiographic signal and the photoelectric pulse wave signal, delay time obtaining sections respectively that obtain a delay time of the electrocardiographic signal and of the photoelectric pulse wave signal, peak correctors respectively that correct the peaks of the electrocardiographic signal and the photoelectric pulse wave signal based on the delay time of the electrocardiographic signal and the photoelectric pulse wave signal, and a pulse wave propagation time measurement section that obtains a pulse wave propagation time from a time difference between the corrected peaks of the electrocardiographic signal and the photoelectric pulse wave signal.

20 Claims, 9 Drawing Sheets

(51) Int. Cl.
  *A61B 5/0245* (2006.01)
  *A61B 5/0452* (2006.01)
  *A61B 5/0456* (2006.01)
  *A61B 5/024* (2006.01)
  *A61B 5/00* (2006.01)

(52) U.S. Cl.
  CPC .......... *A61B 5/0452* (2013.01); *A61B 5/0456* (2013.01); *A61B 5/7289* (2013.01)

(56) References Cited

U.S. PATENT DOCUMENTS

| | | |
|---|---|---|
| 6,558,351 B1 | 5/2003 | Steil et al. |
| 2005/0261593 A1 | 11/2005 | Zhang et al. |
| 2008/0249382 A1 | 10/2008 | Oh et al. |
| 2012/0197140 A1 | 8/2012 | Okuda |
| 2013/0267859 A1 | 10/2013 | Okuda et al. |

FOREIGN PATENT DOCUMENTS

| | | |
|---|---|---|
| JP | 2003522558 A | 7/2003 |
| JP | 2004-081285 A | 3/2004 |
| JP | 2012-101027 A | 5/2012 |
| WO | WO 0074753 A1 | 12/2000 |
| WO | WO 2007/094464 A1 | 6/2007 |
| WO | WO 2011/048729 A1 | 4/2011 |

OTHER PUBLICATIONS

Written Opinion of the International Searching Authority issued for PCT/JP2014/051464, date of mailing Mar. 11, 2014.

\* cited by examiner

PULSE WAVE PROPAGATION TIME MEASUREMENT DEVICE

CROSS-REFERENCE TO RELATED APPLICATIONS

The present application is a continuation of PCT/JP2014/051464 filed Jan. 24, 2014, which claims priority to Japanese Patent Application No. 2013-035546, filed Feb. 26, 2013, the entire contents of each of which are incorporated herein by reference.

FIELD OF THE INVENTION

The present invention relates to pulse wave propagation time measurement devices configured to measure pulse wave propagation times.

BACKGROUND OF THE INVENTION

In recent years, people have been paying more attention to maintenance and improvement of their health than before. People want to readily obtain information such as blood pressure, an electrocardiogram, a heart rate, and so on for health management. As such, Patent Document 1 discloses a portable blood pressure measuring device that measures an electrocardiographic wave and a plethysmogram to obtain a plethysmogram propagation time (pulse wave propagation time), and calculates a maximal blood pressure and a minimal blood pressure. This portable blood pressure measuring device includes an electrocardiographic wave detection means that has one electrode in contact with a biological body surface and detects an electrocardiographic potential (electrocardiographic wave) induced on the above electrode and a plethysmogram detection means that measures a pulse using a photoelectric sensor in contact with the biological body surface; obtains a pulse wave propagation time from a time difference between an R-wave (peak) of the detected electrocardiographic wave and a peak (rising point) of the detected pulse wave; and calculates blood pressures based on a correlation table of the pulse wave propagation times and the blood pressures defined in advance.

Because biological signals of electrocardiographic waves, photoelectric pulse waves, and the like are weak in magnitude and include a lot of noise depending on measurement environments, it is difficult to obtain precise measurement results. As such, a method in which filtering is performed using a frequency filter or the like to improve a signal to noise ratio (S/N ratio) is generally employed. Here, the above-mentioned electrocardiographic wave detection means configuring the portable blood pressure measuring device obtains an electrocardiographic wave signal via a notch filter that cuts AC noise of 50 through 60 Hz and a band pass filer that selectively passes frequency components of the electrocardiographic wave. The plethysmogram detection means extracts pulsation components (plethysmogram signal) via a band pass filter that selectively passes 0.3 to 10 Hz signals as the frequency components of the pulse wave.

Patent Document 1: Japanese Unexamined Patent Application Publication No. 2004-81285

There exists a problem that peaks of an electrocardiographic signal and a photoelectric pulse wave signal are shifted respectively when filtering is performed. To obtain a pulse wave propagation time with high precision, the peak of the electrocardiographic signal and the peak of the photoelectric pulse wave signal need be precisely detected. However, with the above-mentioned portable blood pressure measuring device, the peaks are shifted by the filtering being performed, which raises a risk that the precision in measurement of the pulse wave propagation time is lowered. In particular, filters generally have frequency characteristics (frequency dependency); meanwhile, electrocardiographic signals and photoelectric pulse wave signals have different frequency components from each other. As such, an amount of shift of the peak of the electrocardiographic signal and an amount of shift of the peak of the photoelectric pulse wave signal due to filtering are different from each other in some case. As a result, there arises a risk that the precision in measurement of the pulse wave propagation time is further lowered.

SUMMARY OF THE INVENTION

The present invention has been carried out so as to solve the above-mentioned problems, and an object of the invention is to provide a pulse wave propagation time measurement device capable of measuring a pulse wave propagation time more precisely.

A pulse wave propagation time measurement device according to the present invention includes an electrocardiographic sensor that has an electrocardiographic electrode and detects an electrocardiographic signal; a photoelectric pulse wave sensor that has a light-emitting element and a light-receiving element and detects a photoelectric pulse wave signal; a first signal processing means that performs a signal process including filtering processing on the electrocardiographic signal detected by the electrocardiographic sensor; a second signal processing means that performs a signal process including filtering processing on the photoelectric pulse wave signal detected by the photoelectric pulse wave sensor; a peak detecting means that detects a peak of the electrocardiographic signal on which the signal process has been performed by the first signal processing means and a peak of the photoelectric pulse wave signal on which the signal process has been performed by the second signal processing means; a delay time obtaining means that obtains a delay time of the electrocardiographic signal in the first signal processing means and/or a delay time of the photoelectric pulse wave signal in the second signal processing means; a correcting means that corrects the peak of the electrocardiographic signal detected by the peak detecting means and/or the peak of the photoelectric pulse wave signal detected by the peak detecting means based on the delay time of the electrocardiographic signal obtained by the delay time obtaining means and/or the delay time of the photoelectric pulse wave signal obtained by the delay time obtaining means; and a calculating means that obtains a pulse wave propagation time from a time difference between the peak of the photoelectric pulse wave signal and the peak of the electrocardiographic signal which have been corrected by the correcting means.

With the pulse wave propagation time measurement device according to the present invention, an electrocardiographic signal and a photoelectric pulse wave signal can be obtained at a preferable S/N ratio by performing a signal process including filtering processing. Further, because correction operation is performed on the detected peak of the electrocardiographic signal and/or the detected peak of the photoelectric pulse wave signal corresponding to the delay times of the electrocardiographic signal and the photoelectric pulse wave signal respectively due to the signal processes, the peaks of the electrocardiographic signal and the photoelectric pulse wave signal can be more accurately specified. This makes it possible to measure the pulse wave propagation time more precisely.

In the pulse wave propagation time measurement device according to the present invention, it is preferable that the delay time obtaining means obtain a delay time of the electrocardiographic signal and/or a delay time of the photoelectric pulse wave signal based on frequency components of the electrocardiographic signal and the photoelectric pulse wave signal, respectively.

Through this, even if the first signal processing means and the second signal processing means have frequency characteristics (frequency dependency) and the amounts of shifts of the peaks (delay times) vary depending on the respective frequency characteristics of the electrocardiographic signal and the photoelectric pulse wave signal, the respective shifts can be appropriately corrected. This makes it possible to measure the pulse wave propagation time more precisely.

In the pulse wave propagation time measurement device according to the present invention, it is preferable that the above frequency component be defined corresponding to a pulse rate obtained from the photoelectric pulse wave signal or a heart rate obtained from the electrocardiographic signal.

Through this, by making use of a pulse rate obtained from the photoelectric pulse wave signal or a heart rate obtained from the electrocardiographic signal, it is possible to obtain the above-mentioned frequency components relatively with ease without performing a special or dedicated process (for example, FFT or the like).

It is preferable that the pulse wave propagation time measurement device according to the present invention further include an inverting means that inverts polarity of the electrocardiographic signal detected by the electrocardiographic sensor.

With this, even in a case where portions of a biological body with which electrocardiographic electrodes make contact are reversed, a user has a physical constitution such that an R-wave (peak) included in an electrocardiographic signal is formed upside down, or the like, inverting the polarity of the electrocardiographic signal makes it possible to correctly detect the peak. As such, the pulse wave propagation time can be measured more accurately.

In the pulse wave propagation time measurement device according to the present invention, it is preferable, in the case where a plurality of peaks of the electrocardiographic signal having different polarities are detected, that the calculating means take a peak which forms the longest pulse wave propagation time within a predetermined time as a true peak among the plurality of peaks.

This makes it possible to correctly detect a peak even in a case where portions of a biological body with which electrocardiographic electrodes make contact are reversed, a user has a physical constitution such that an R-wave (peak) included in an electrocardiographic signal is formed upside down, or the like. Further, because an electrocardiographic waveform differs depending on a measurement portion, a physical constitution, or the like, and deforms when experiencing filtering, the R-wave can be generated upside down in some case; however, even in this case, the peak can be correctly detected. As such, the pulse wave propagation time can be measured more precisely.

In the pulse wave propagation time measurement device according to the present invention, it is preferable that the calculating means determine, in the case where an obtained pulse wave propagation time does not fall within a predetermined time, the obtained pulse wave propagation time being an error.

Normally, a pulse wave propagation time which is a time difference between an electrocardiographic wave and a photoelectric pulse wave is approximately 0.1 to 0.3 seconds, and its change width is not so large and is approximately 10%. In this case, if an obtained pulse wave propagation time does not fall within a predetermined time, the measurement result is taken as an error, thereby making it possible to prevent an erroneous pulse wave propagation time measurement.

In the pulse wave propagation time measurement device according to the present invention, it is preferable that the calculating means determine, in the case where an obtained pulse wave propagation time does not fall within a predetermined time, the detected peak of the electrocardiographic signal being an error when a change rate of a heartbeat interval is larger than a change rate of a pulse interval or the detected peak of the photoelectric pulse wave signal being an error when the change rate of the pulse interval is larger than the change rate of the heartbeat interval.

Also in this case, if an obtained pulse wave propagation time does not fall within a predetermined time, an erroneous pulse wave propagation time measurement can be prevented from being carried out. Further in this case, because it is possible to specify which of the electrocardiographic signal peak and the photoelectric pulse wave signal peak is an erroneous one, data of a pulse interval, a heartbeat interval, or the like, for example, can be obtained using the signal which is detected as being not erroneous.

In the pulse wave propagation time measurement device according to the present invention, it is preferable that, in the case where an obtained pulse wave propagation time does not fall within a predetermined time, the calculating means search for a combination of an electrocardiographic signal peak and a photoelectric pulse wave signal peak, from among the combinations of the detected peak and one or more additional electrocardiographic signal peaks present near the detected peak, and the detected peak and one or more additional photoelectric pulse wave signal peaks present near the detected peak, that allows a pulse wave propagation time to fall within the predetermined time, select a combination if a plurality of the combinations being present, considering at least one of the change rate of a pulse wave propagation time, amplitude of the electrocardiographic signal peak and the change rate of the amplitude thereof, amplitude of the photoelectric pulse wave signal peak and the change rate of the amplitude thereof, the change rate of the heartbeat interval, and the change rate of the pulse interval, and then obtain a pulse wave propagation time.

With this, even in a case where a measurement value of a pulse wave propagation time does not fall within a predetermined time, a pulse wave propagation time which is more likely to be accurate can be obtained.

According to the present invention, a pulse wave propagation time can be measured more precisely.

DETAILED DESCRIPTION OF THE EXEMPLARY EMBODIMENTS

Figure 1:
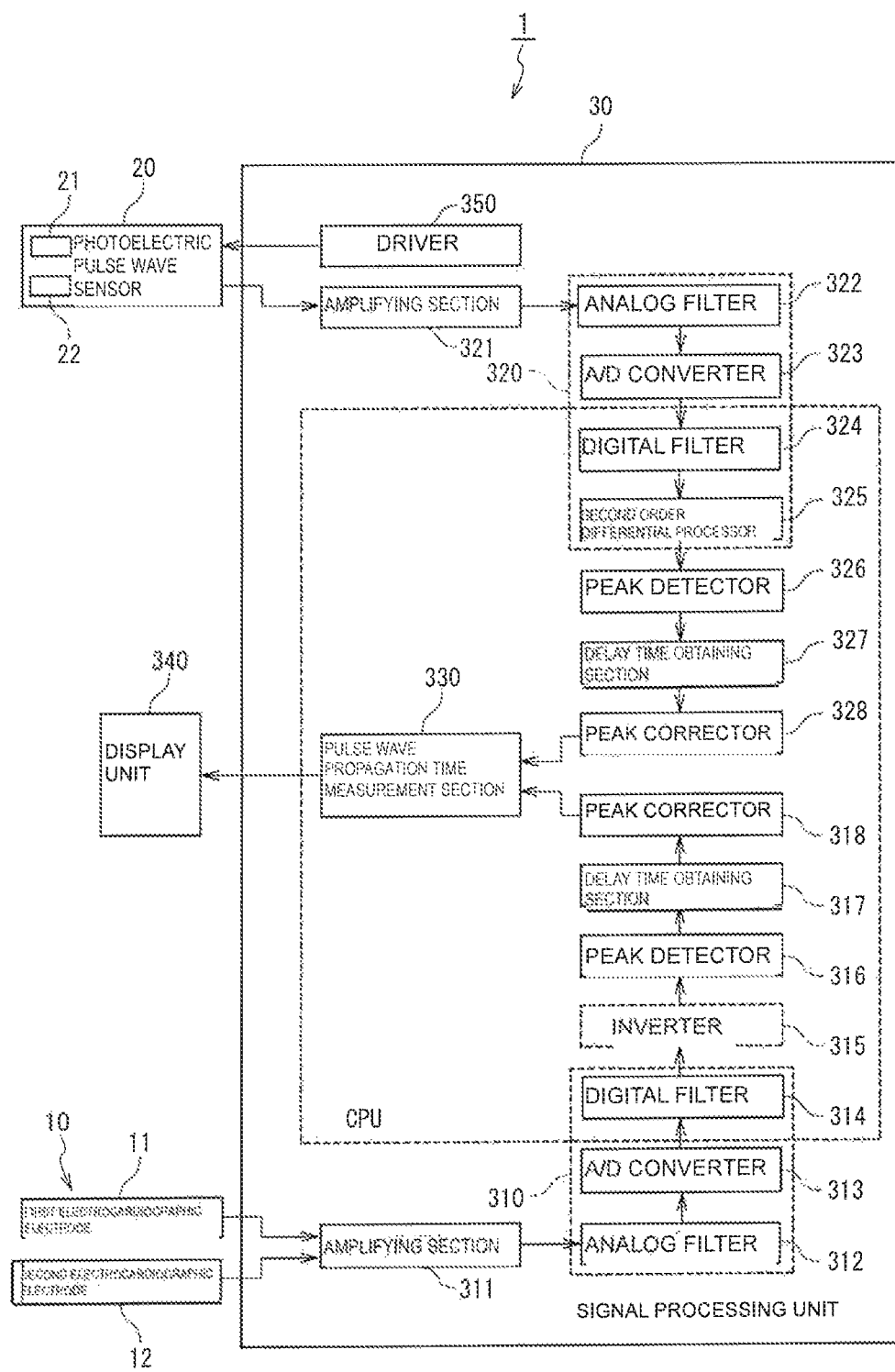
FIG. 1 is a block diagram illustrating a configuration of a pulse wave propagation time measurement device according to an embodiment.

Hereinafter, preferred embodiments of the present invention will be described with reference to the drawings. Note that in the drawings, identical elements are assigned the same reference numerals and redundant descriptions thereof will be omitted.

First, a configuration of a pulse wave propagation time measurement device 1 will be described with reference to FIG. 1. FIG. 1 is a block diagram illustrating the configuration of the pulse wave propagation time measurement device 1.

Figure 4:
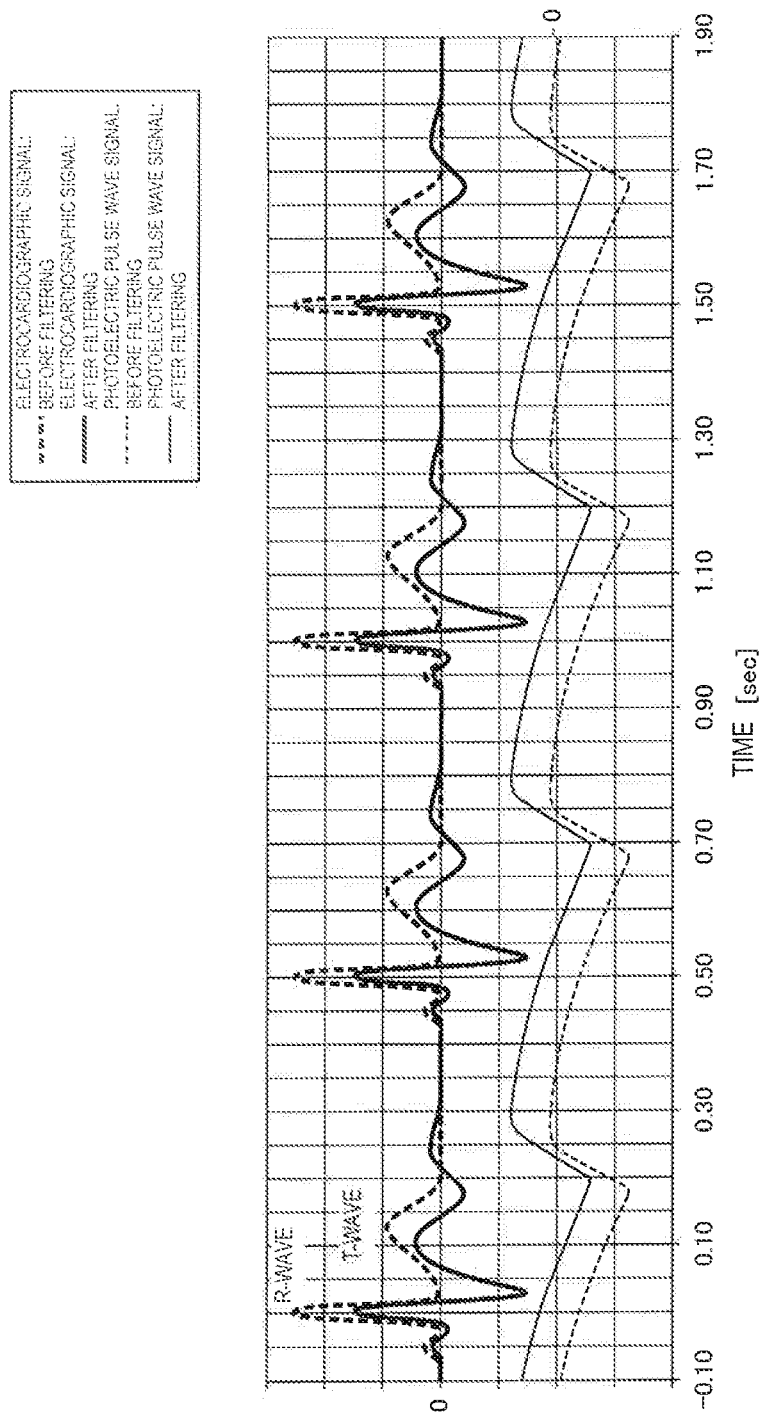
FIG. 4 is a diagram illustrating electrocardiographic waveforms before and after filtering, and photoelectric pulse waveforms before and after filtering.
Figure 5:
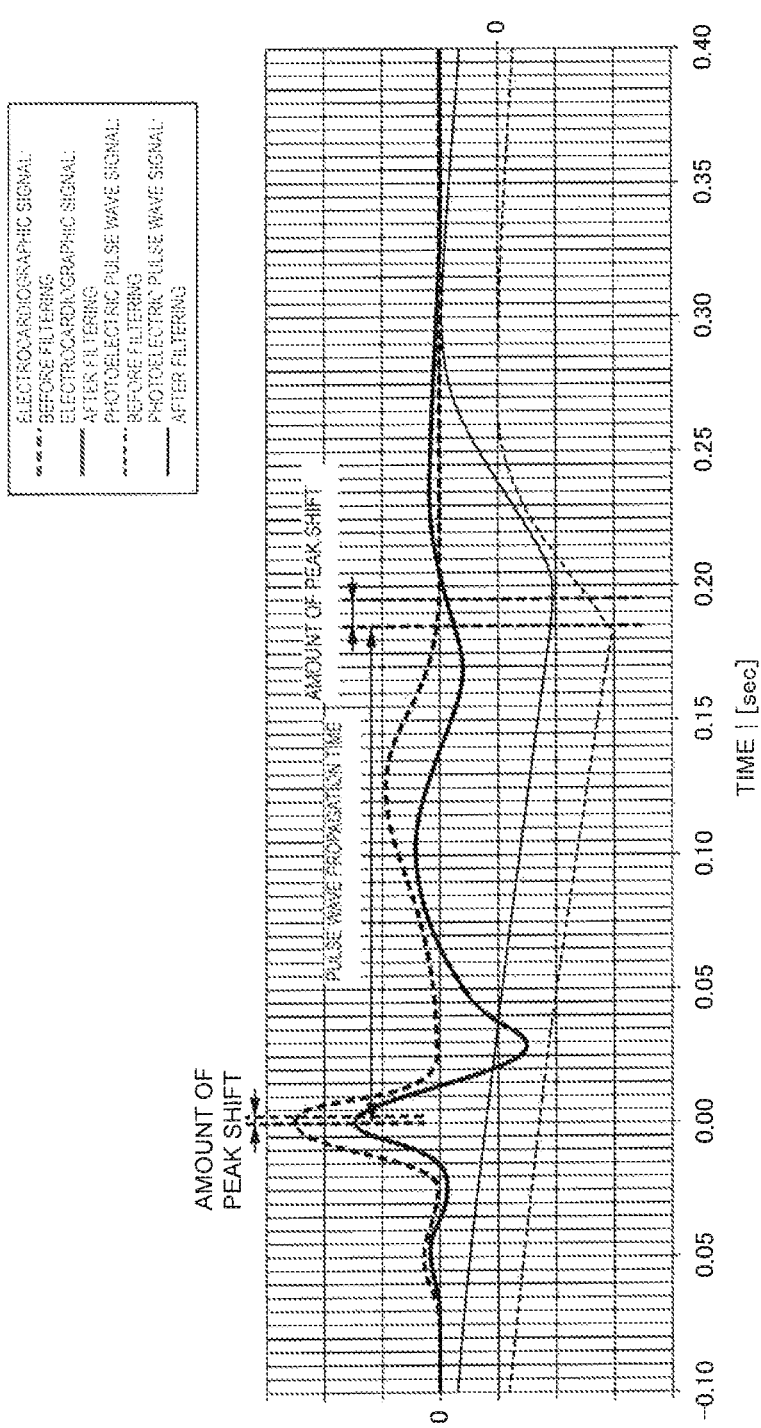
FIG. 5 is a partially enlarged diagram of the diagram in FIG. 4.

The pulse wave propagation time measurement device 1 detects an electrocardiographic signal and a photoelectric pulse wave signal, and measures a pulse wave propagation time from a time difference between an R-wave peak of the detected electrocardiographic signal (electrocardiographic wave) and a peak (rising point) of the detected photoelectric pulse wave signal (pulse wave) (see FIGS. 4 and 5). Accordingly, the pulse wave propagation time measurement device 1 includes an electrocardiographic sensor 10 for detecting electrocardiographic signals, a photoelectric pulse wave sensor 20 for detecting photoelectric pulse wave signals, and a signal processing unit 30 configured to measure a pulse wave propagation time and the like based on the detected electrocardiographic and photoelectric pulse wave signals. In the following, each constituent element will be described in detail.

The electrocardiographic sensor 10 includes a pair of a first electrocardiographic electrode 11 and a second electrocardiographic electrode 12, and detects electrocardiographic signals using the first electrocardiographic electrode 11 and the second electrocardiographic electrode 12. The first electrocardiographic electrode 11 and the second electrocardiographic electrode 12 are respectively attached being in contact with, for example, right and left hands, right and left arms, or the like of a human body. As an electrode material of the first electrocardiographic electrode 11 and second electrocardiographic electrode 12, metal (metal which has excellent corrosion resistance and hardly causes metallic allergy, such as stainless steel, Au, or the like, is preferable), conductive gel, conductive rubber, conductive cloth, or the like is preferably used. As another material for the first electrocardiographic electrode 11 and the second electrocardiographic electrode 12, for example, conductive plastic, a capacitive coupling electrode, or the like can be used. The first electrocardiographic electrode 11 and the second electrocardiographic electrode 12 are respectively connected to the signal processing unit 30 via cables, and output electrocardiographic signals to the signal processing unit 30 via the cables.

The photoelectric pulse wave sensor 20 is a sensor configured to optically detect a photoelectric pulse wave signal by making use of the light absorption characteristics of hemoglobin in bloodstream. As such, the photoelectric pulse wave sensor 20 is so configured as to include a light-emitting element 21 and a light-receiving element 22.

The light-emitting element 21 emits light in response to a drive signal in pulse form outputted from a driver 350 of the signal processing unit 30. As the light-emitting element 21, an LED, a vertical cavity surface emitting laser (VCSEL), a resonator type LED, or the like can be used, for example. The driver 350 generates and outputs the drive signal in pulse form for driving the light-emitting element 21.

The light-receiving element 22 outputs a detection signal in accordance with the intensity of light that is emitted from the light-emitting element 21, passes through a human body such as a fingertip or reflects off the human body, and enters the light-receiving element 22. As the light-receiving element 22, for example, a photodiode, a phototransistor, or the like is preferably used. In the present embodiment, a photodiode is used as the light-receiving element 22. The light-receiving element 22 is connected to the signal processing unit 30, and the detection signal (photoelectric pulse wave signal) obtained by the light-receiving element 22 is outputted to the signal processing unit 30.

As described above, the electrocardiographic sensor 10 (first electrocardiographic electrode 11, second electrocardiographic electrode 12) and the photoelectric pulse wave sensor 20 are respectively connected to the signal processing unit 30, and the detected electrocardiographic and photoelectric pulse wave signals are inputted to the signal processing unit 30.

The signal processing unit 30 processes the inputted electrocardiographic signal so as to measure a heart rate, a heartbeat interval, and the like. Further, the signal processing unit 30 processes the inputted photoelectric pulse wave signal so as to measure a pulse rate, a pulse interval, and the like. Furthermore, the signal processing unit 30 measures a pulse wave propagation time and the like from a time difference between an R-wave peak of the electrocardiographic signal (electrocardiographic wave) and a peak (rising point) of the photoelectric pulse wave signal (pulse wave) which have been detected (see FIGS. 4 and 5). At this time, the signal processing unit 30 corrects shifts (delays) of the respective peaks in a first signal processing section 310 and a second signal processing section 320, which will be explained later, so as to measure the pulse wave propagation time with high precision.

As such, the signal processing unit 30 includes amplifying sections 311 and 321, the first signal processing section 310, the second signal processing section 320, peak detectors 316 and 326, delay time obtaining sections 317 and 327, peak correctors 318 and 328, and a pulse wave propagation time measurement section 330. Further, the first signal processing section 310 includes an analog filter 312, an A/D converter 313, and a digital filter 314. Meanwhile, the second signal processing section 320 includes an analog filter 322, an A/D converter 323, a digital filter 324, and a second order differential processor 325.

Here, of the above-mentioned constituent elements, the digital filters 314 and 324, the second order differential processor 325, the peak detectors 316 and 326, the delay time obtaining sections 317 and 327, the peak correctors 318 and 328, and the pulse wave propagation time measurement section 330 are configured of a CPU which executes arithmetic operations, a ROM which stores programs, data, and the like for making the CPU execute the arithmetic operations, a RAM which temporarily stores various data such as arithmetic operation results, and so on. In other words, the programs stored in the ROM are executed by the CPU so as to realize functions of the above constituent elements.

The amplifying section 311 is configured of an amplifier using an operational amplifier or the like, for example, and amplifies an electrocardiographic signal detected by the electrocardiographic sensor 10 (first electrocardiographic electrode 11, second electrocardiographic electrode 12). The electrocardiographic signal amplified by the amplifying section 311 is outputted to the first signal processing section 310. Likewise, the amplifying section 321 is configured of an amplifier using an operational amplifier or the like, for example, and amplifies a photoelectric pulse wave signal detected by the photoelectric pulse wave sensor 20. The photoelectric pulse wave signal amplified by the amplifying section 321 is outputted to the second signal processing section 320.

The first signal processing section 310 includes, as described above, the analog filter 312, the A/D converter 313, and the digital filter 314, and extracts a pulsation component by performing filtering processing on the electrocardiographic signal having been amplified in the amplifying section 311. In other words, the first signal processing section 310 functions as a first signal processing means that is claimed in the claims.

The second signal processing section 320 includes, as described above, the analog filter 322, the A/D converter 323, the digital filter 324, and the second order differential processor 325, and extracts a pulsation component by performing filtering processing as well as performing a second order differential processing on the photoelectric pulse wave signal having been amplified in the amplifying section 321. In other words, the second signal processing section 320 functions as a second signal processing means that is claimed in the claims.

The analog filters 312, 322 and the digital filters 314, 324 remove components (noise) other than the frequency components that characterize the electrocardiographic signal and the photoelectric pulse wave signal, and perform filtering to improve the S/N ratios. To be more specific, frequency components of 0.1 to 200 Hz are generally dominant in an electrocardiographic signal, and frequency components in the vicinity of 0.1 to tens of Hz are dominant in a photoelectric pulse wave signal. Accordingly, by performing filtering processing with the analog filters 312, 322 such as a low pass filter, a band pass filter, or the like as well as performing filtering processing with the digital filters 314, 324 and selectively passing only the signals that are within the above frequency ranges, the S/N ratios can be improved.

In the case where only the extraction of a pulsation component is aimed at (in other words, an electrocardiographic waveform and the like need not be obtained), components other than the pulsation component may be blocked by making a pass frequency range smaller so as to enhance noise resistance. Further, both of the analog filters 312, 322 and the digital filters 314, 324 are not necessarily needed to be provided, and the configuration may be such that any one of a set of the analog filters 312, 322 and a set of the digital filters 314, 324 is provided. The electrocardiographic signal having experienced the filtering processing performed by the analog filter 312 and the digital filer 314 is outputted to the peak detector 316. Likewise, the photoelectric pulse wave signal having experienced the filtering processing performed by the analog filter 322 and the digital filer 324 is outputted to the second order differential processor 325.

The second order differential processor 325 obtains a second order differential pulse wave (acceleration pulse wave) signal through performing second order differential on the photoelectric pulse wave signal. The obtained acceleration pulse wave signal is outputted to the peak detector 326. Since a peak (rising point) of a photoelectric pulse wave signal does not change clearly, the peak thereof is hard to detect in some case. As such, it is preferable to detect the peak after converting the photoelectric pulse wave to an acceleration pulse wave; however, the second order differential processor 325 is not necessarily required to be provided, and a configuration in which the processor is omitted may be employed.

The peak detector 316 detects a peak (R-wave) of the electrocardiographic signal that has experienced the signal processing (a pulsation component has been extracted) performed by the first signal processing section 310. At this time, the peak detector 316 detects peaks at both the upper and lower sides of the electrocardiographic wave (electrocardiographic signal). The reason for this is as follows. That is, in the case where portions with which the first electrocardiographic electrode 11 and the second electrocardiographic electrode 12 make contact are reversed, an R-wave (peak) is formed upside down depending on a physical constitution of the user, or the like, there arises a risk that the R-wave (peak) cannot be detected or a peak other than the R-wave (for example, T-wave or the like) is erroneously detected as an R-wave. Accordingly, in order to correctly detect the R-wave even in the above case, the peak detector 316 is configured to detect peaks at both the upper and lower sides of an electrocardiographic wave so as to automatically determine at which side of the electrocardiographic wave an R-wave included in the electrocardiographic waveform is formed (details will be explained later).

Meanwhile, the peak detector 326 detects a peak (rising point) of the photoelectric pulse wave signal (acceleration pulse wave) that has experienced the filtering processing performed by the second signal processing section 320. In other words, the peak detectors 316 and 326 function as a peak detecting means that is claimed in the claims. The peak detector 316 and the peak detector 326 respectively detect peaks within normal ranges of the heartbeat interval and the pulse interval (details will be explained later), and store information such as peak time, peak amplitude, and the like of every detected peak in the RAM or the like.

Since the filters (analog filters 312 and 322, digital filters 314 and 324) have frequency characteristics, it is necessary to analyze the frequency components of the electrocardiographic signal and the photoelectric pulse wave signal and perform correction with respect to each peak shift time (delay time) based on the stated frequency components so as to measure a pulse wave propagation time more precisely. Further, a delay of signal is also generated when the differential processing is performed in the second order differential processor 325. As such, the delay time obtaining section 317 obtains a delay time of the electrocardiographic signal in the first signal processing section 310 (analog filter 312, digital filter 314). Likewise, the delay time obtaining section 327 obtains a delay time of the photoelectric pulse wave signal in the second signal processing section 320 (analog filter 322, digital filter 324, second order differential processor 325). In other words, the delay time obtaining sections 317 and 327 function as a delay time obtaining means that is claimed in the claims.

To be more specific, the delay time obtaining sections 317 and 327 respectively obtain a delay time of the electrocardiographic signal (amount of peak shift) and a delay time of the photoelectric pulse wave signal (amount of peak shift) based on the respective frequency components of the electrocardiographic signal and the photoelectric pulse wave signal. Note that a table in which a relationship between the frequency components and the delay times is defined (delay time table) is stored in the ROM or the like in advance. Accordingly, the delay time obtaining sections 317 and 327 respectively search the delay time table using a pulse rate derived from a peak interval of the photoelectric pulse wave and a heart rate derived from a peak interval of the electrocardiographic signal (frequency component index value), so as to obtain a delay time of the electrocardiographic signal in the first signal processing section 310 and a delay time of the photoelectric pulse wave signal in the second signal processing section 320, for example. The peak of the electrocardiographic signal detected by the peak detector 316 and the peak of the photoelectric pulse wave signal (acceleration pulse wave) detected by the peak detector 326 as well as the delay time of the peak obtained by the delay time obtaining section 317 and the delay time of the peak obtained by the delay time obtaining section 327, are outputted to the peak correctors 318 and 328, respectively.

The peak corrector 318 corrects the peak of the electrocardiographic signal detected by the peak detector 316 based on the delay time of the electrocardiographic signal obtained by the delay time obtaining section 317. Likewise, the peak corrector 328 corrects the peak of the photoelectric pulse wave signal (acceleration pulse wave signal) detected by the peak detector 326 based on the delay time of the photoelectric pulse wave signal obtained by the delay time obtaining section 327. In other words, the peak correctors 318 and 328 function as a correcting means that is claimed in the claims. The post-correction electrocardiographic signal peak and the post-correction photoelectric pulse wave (acceleration pulse wave) peak are outputted to the pulse wave propagation time measurement section 330. Note that an electrocardiographic signal has low frequency dependency. In other words, in an electrocardiographic signal, even if a pulse rate (heart rate) changes, the frequency component of the R-wave hardly changes. Accordingly, it is not necessarily required to provide the delay time obtaining section 317 and the peak corrector 318, and a configuration in which they are omitted may be employed.

The pulse wave propagation time measurement section 330 obtains a pulse wave propagation time from an interval (time difference) between the R-wave (peak) of the electrocardiographic signal corrected by the peak corrector 318 and the peak (rising point) of the photoelectric pulse wave signal (acceleration pulse wave) corrected by the peak corrector 328. In other words, the pulse wave propagation time measurement section 330 functions as a calculating means that is claimed in the claims. FIG. 4 is a diagram illustrating electrocardiographic waveforms before and after filtering, and photoelectric pulse waveforms before and after filtering. Further, FIG. 5 is a partially enlarged diagram of the diagram in FIG. 4, and illustrates a pulse wave propagation time obtained from an interval between the post-correction electrocardiographic signal R-wave (peak) and the post-correction photoelectric pulse wave signal (acceleration pulse wave) peak. Note that in FIGS. 4 and 5, waveforms of the electrocardiographic signal and the photoelectric pulse wave after filtering (before correction) are indicated by solid lines, while waveforms of the electrocardiographic signal and the photoelectric pulse wave before filtering (which are the same as the waveforms after correction) are indicated by broken lines.

The pulse wave propagation time measurement section 330 determines that, in the case where a plurality of peaks having different polarities are detected in the electrocardiographic signal, a peak which forms the longest pulse wave propagation time within a predetermined time (for example, no more than approximately 0.3 seconds, although a pulse wave propagation time varies depending on a measurement portion) is a true peak. As described above, the peak detector 316 detects peaks at both the upper and lower sides of an electrocardiographic wave. However, in the pulse wave propagation time measurement section 330, in the case where a peak is detected at only one side (upper or lower side) thereof and the peak interval takes a period equivalent to the heartbeat, the detected peak is determined to be an R-wave, and in the case where peaks are detected at both the upper and lower sides thereof, a peak which forms a longer pulse wave propagation time than the other within a predetermined range (for example, no more than 0.3 seconds) is determined to be an R-wave (see FIG. 6). Whether or not the above-mentioned period is equivalent to the heartbeat is determined in the following manner. That is, the determination is made considering whether or not that period is within a typical range as a heartbeat interval (for example, 0.3 to 1.5 seconds), a change rate with respect to the heartbeat intervals of immediately prior several heartbeats does not become larger than a predetermined value, the value of the period is substantially the same as the pulse interval, and so on.

Figure 6:
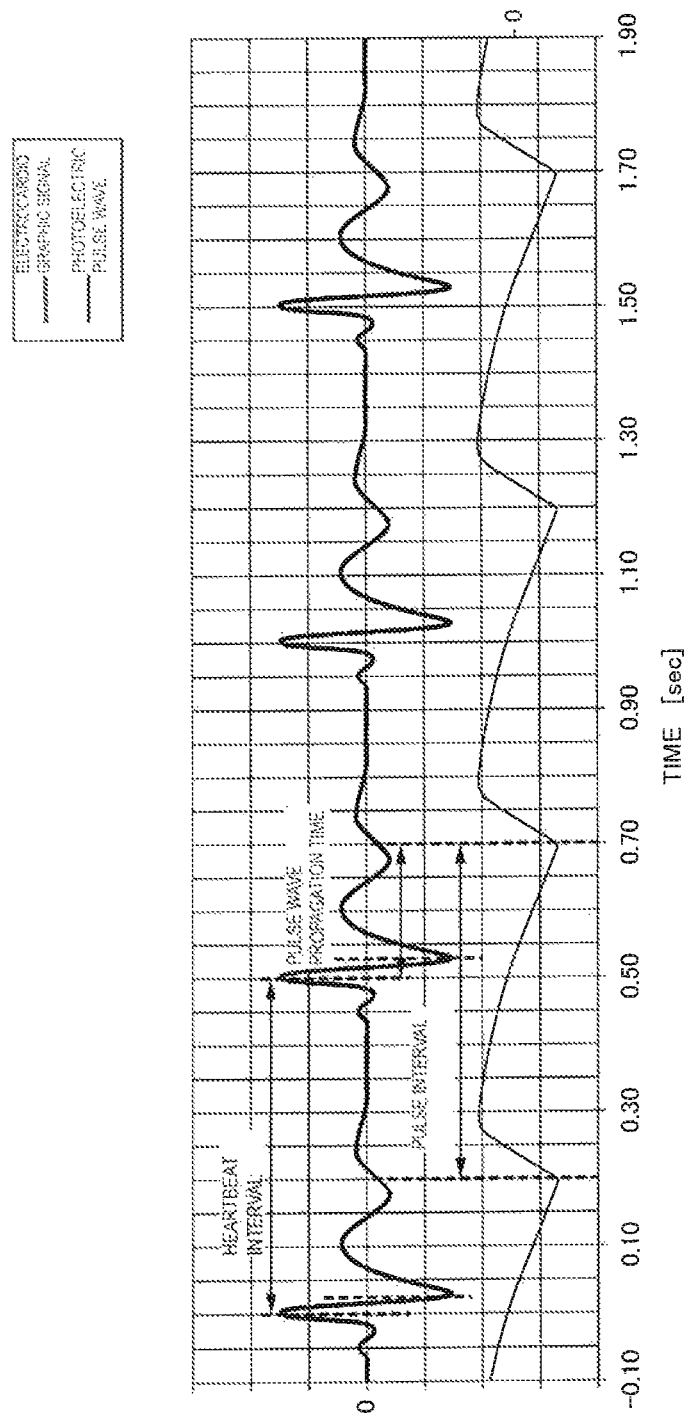
FIG. 6 is a diagram illustrating a heartbeat interval, a pulse interval, and a pulse wave propagation time in the case where peaks are formed at the upper and lower sides of an electrocardiographic wave.

As shown in FIG. 6, for example, depending on filtering processing, the physical constitution of a user, portions to which the first and second electrocardiographic electrodes 11 and 12 are attached, or the like, R-wave peaks are formed at the lower side as well in some case. In this case, the peaks at the lower side appear later compared to the peaks at the upper side. Accordingly, a pulse wave propagation time calculated using a lower side peak becomes shorter than a pulse wave propagation time calculated using an upper side peak. A peak other than the R-wave such as a T-wave or the like can be erroneously detected; and in a case where a peak other than the R-wave is used, a pulse wave propagation time is largely shifted. As such, in the case where peaks are detected at both the upper and lower sides, the pulse wave propagation time measurement section 330 determines that a peak which forms a longer pulse wave propagation time than the other within a predetermined range is an R-wave.

Further, in the case where an obtained pulse wave propagation time does not fall within the predetermined range, the pulse wave propagation time measurement section 330 determines the electrocardiographic R-wave peak and the photoelectric pulse wave (acceleration pulse wave) peak being noise and takes the heartbeat interval, the pulse interval, the pulse wave propagation time, and the like as obtainment errors. In other words, in the case where an obtained pulse wave propagation time does not fall within a predetermined range, there is a high possibility that noise is erroneously detected as an electrocardiographic R-wave peak and/or a photoelectric pulse wave (acceleration pulse wave) peak. As such, in the case where the erroneously detected peak cannot be specified, both the peaks are taken as noise, and the heartbeat interval, the pulse interval, and the pulse wave propagation time having been obtained from those peaks are all taken as obtainment errors.

Figure 7:
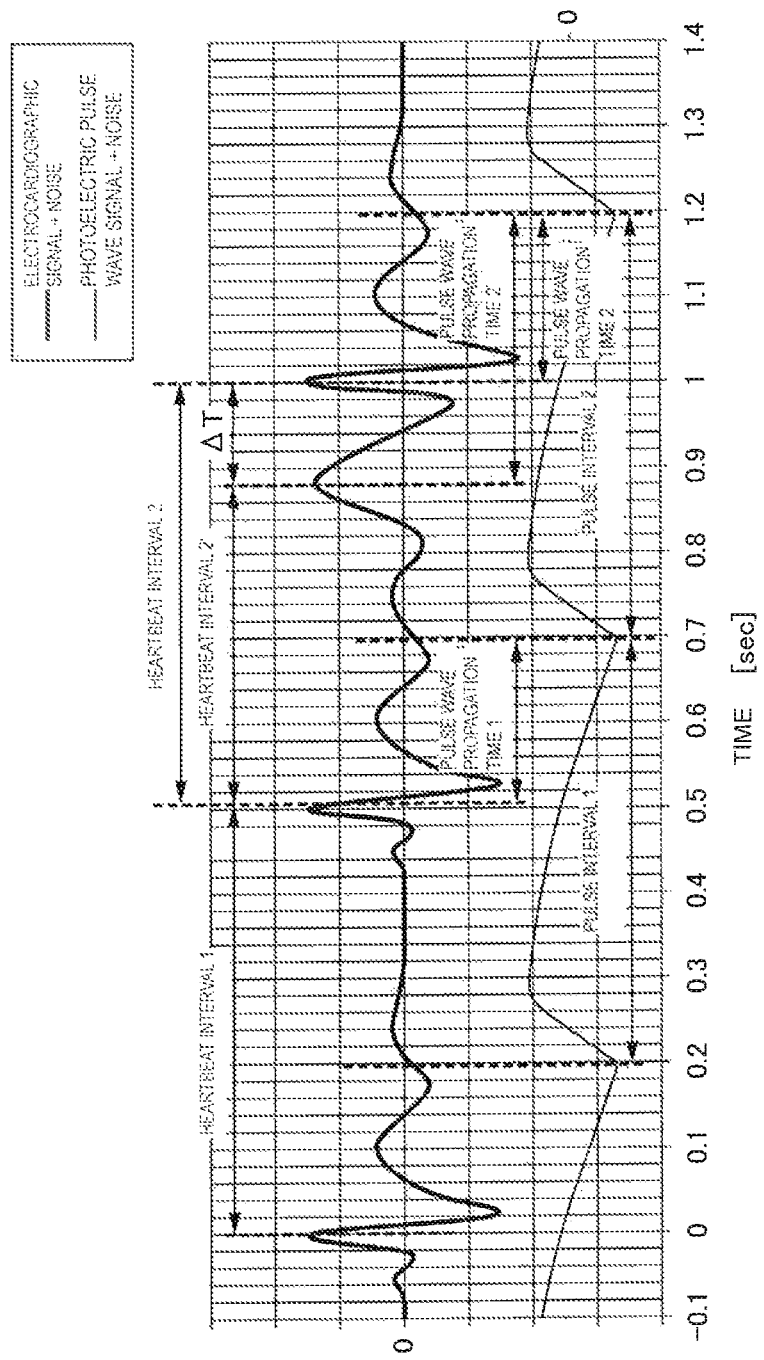
FIG. 7 is a diagram illustrating an example of a peak detection error due to noise.

FIG. 7 is a diagram illustrating an example in which noise included in an electrocardiographic signal is erroneously detected as an electrocardiographic R-wave peak. In the example shown in FIG. 7, a heartbeat interval 2' is shorter than a real interval (heartbeat interval 2) by ΔT due to the erroneous detection. Meanwhile, a pulse wave propagation time 2' is longer than a real time (pulse wave propagation time 2) by ΔT due to the erroneous detection. Normally, a pulse wave propagation time is shorter than a heartbeat interval (a pulse wave propagation time is typically no more than approximately 0.3 seconds, although it varies depending on a measurement portion), and a variation width thereof is small (approximately 10%). Accordingly, even in a case where the heartbeat interval 2' (=heartbeat interval 2−ΔT) cannot be determined to be an erroneous detection because it is within a typical range as a heartbeat interval (for example, 0.3 to 1.5 seconds) and a change rate with respect to the heartbeat intervals of immediately prior several heartbeats (average value) is smaller than a predetermined value, the heartbeat interval 2' is determined to be an erroneous detection if the pulse wave propagation time 2' (=pulse wave propagation time 2+ΔT) is not within a predetermined range or a change rate of the pulse wave propagation time is larger than a predetermined value. Upon the erroneous detection being determined, the electrocardiographic R-wave peak and the photoelectric pulse wave (acceleration pulse wave) peak are determined to be noise, and then the heartbeat interval, the pulse interval, and the pulse wave propagation time are taken as obtainment errors.

Note that the pulse wave propagation time measurement section 330 determines, in the case where an obtained pulse wave propagation time does not fall within a predetermined time, that the detected electrocardiographic signal peak is an error if a change rate of the heartbeat interval is larger than that of the pulse interval and that the detected photoelectric pulse wave signal peak is an error if the change rate of the pulse interval is larger than that of the heartbeat interval. In other words, in the case where the change rate of the heartbeat interval is larger than that of the pulse interval, because there is a high possibility that the electrocardiographic R-wave peak is erroneously detected, the pulse wave propagation time measurement section 330 determines the electrocardiographic R-wave peak being noise and takes the heartbeat interval and the pulse wave propagation time as obtainment errors. Meanwhile, in the case where the change rate of the heartbeat interval is smaller than that of the pulse interval, because there is a high possibility that the photoelectric pulse wave (acceleration pulse wave) peak is erroneously detected, the pulse wave propagation time measurement section 330 determines the photoelectric pulse wave (acceleration pulse wave) peak being noise and takes the pulse interval and the pulse wave propagation time as obtainment errors.

The pulse wave propagation time measurement section 330 calculates, from an electrocardiographic signal, a heart rate, a heartbeat interval, a heartbeat interval change rate, and the like, for example, in addition to a pulse wave propagation time. Likewise, the pulse wave propagation measurement section 330 calculates, from a photoelectric pulse wave signal (acceleration pulse wave), a pulse rate, a pulse interval, a pulse interval change rate, and the like. Measurement data including the pulse wave propagation time, heart rate, heartbeat interval, pulse rate, pulse interval, electrocardiographic wave, photoelectric pulse wave, acceleration pulse wave, and the like which have been calculated is outputted to a display unit 340 or the like. Note that the measurement data of the obtained pulse wave propagation time, heart rate, pulse rate, and the like may be accumulated and stored in the above-mentioned RAM or the like, for example, and outputted to a personal computer or the like after the measurement so as to be confirmed.

The display unit 340 is configured of, for example, a liquid crystal display (LCD) or the like, and displays the measurement data (measurement result) of the obtained pulse wave propagation time, heart rate, pulse rate, and the like.

Figure 2:
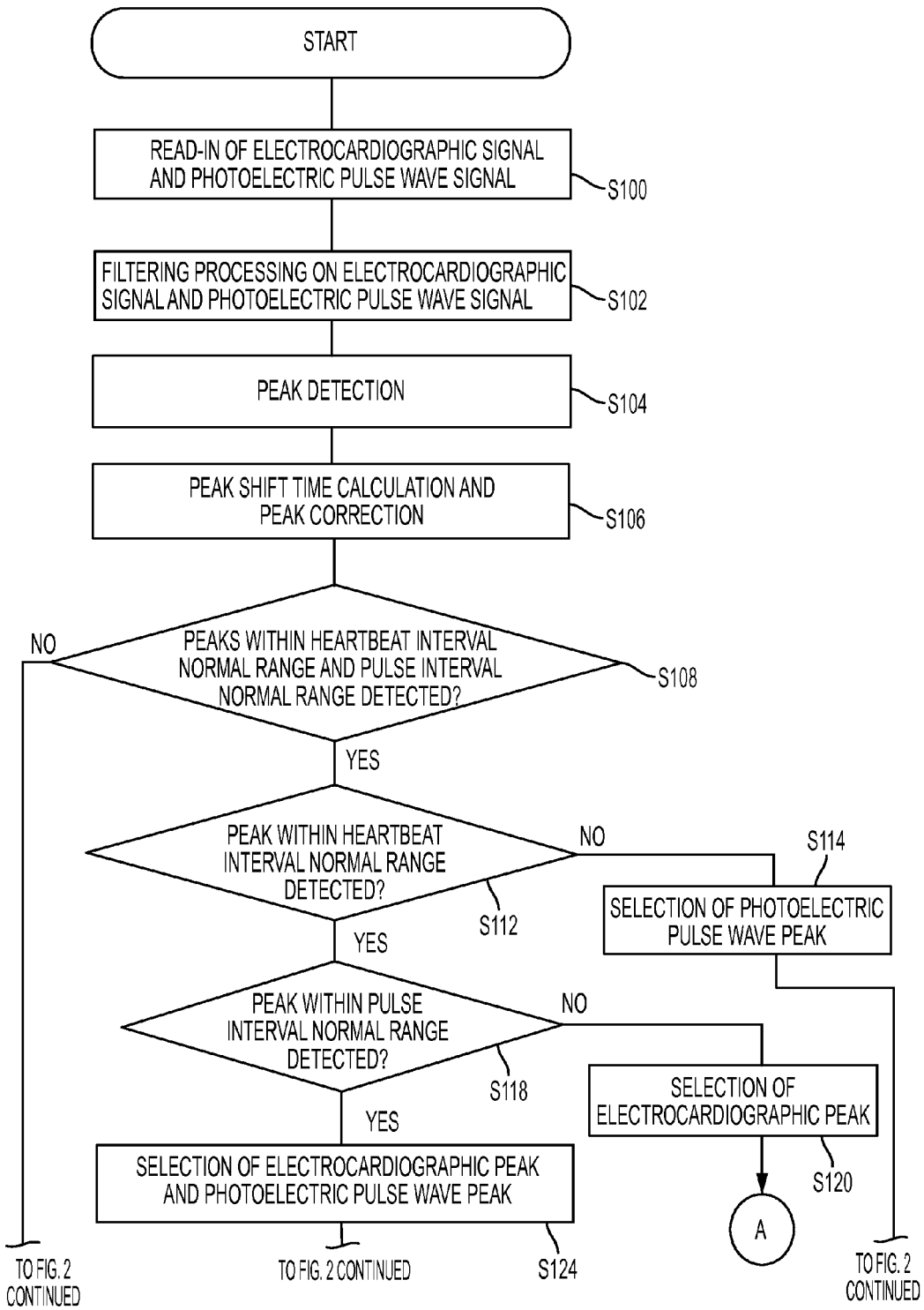
FIG. 2 is a flowchart illustrating a sequence of steps in a pulse wave propagation time measurement process carried out by a pulse wave propagation time measurement device according to an embodiment.
Figure 2:
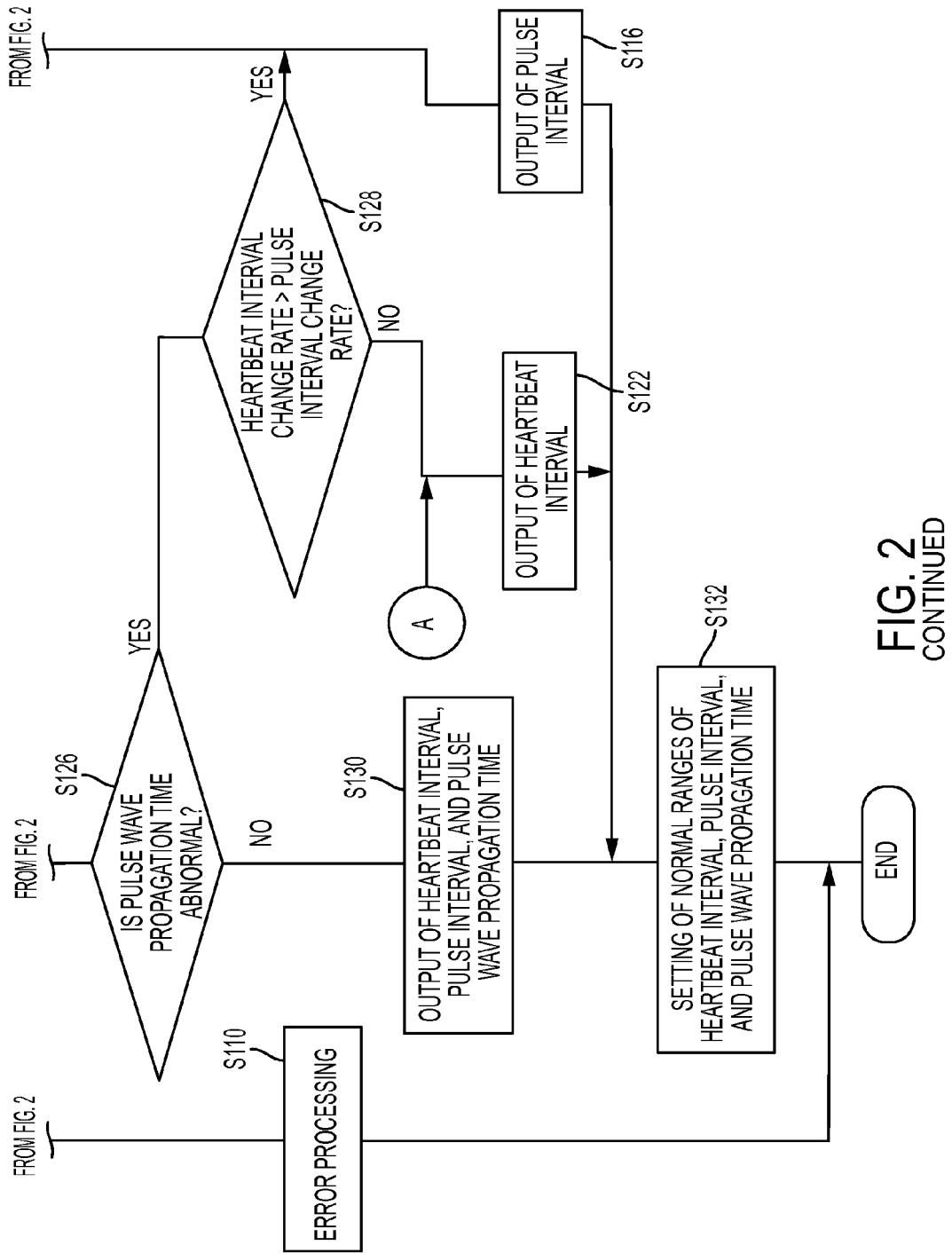

Next, with reference to FIG. 2, operations of the pulse wave propagation time measurement device 1 will be described. FIG. 2 is a flowchart illustrating a sequence of steps in a pulse wave propagation time measurement process carried out by the pulse wave propagation time measurement device 1. This process is executed by the signal processing unit 30 at a predetermined timing.

In step S100, an electrocardiographic signal (electrocardiographic waveform) detected by the electrocardiographic sensor 10 and a photoelectric pulse wave signal (photoelectric pulse waveform) detected by the photoelectric pulse wave sensor 20 are read in. In the subsequent step S102, filtering processing is performed on the electrocardiographic signal (electrocardiographic waveform) and the photoelectric pulse wave signal (photoelectric pulse waveform) having been read in in step S100. Further, an acceleration pulse wave is obtained through performing second order differential on the photoelectric pulse wave signal.

Next, in step S104, peaks of the electrocardiographic signal and the photoelectric pulse wave signal (acceleration pulse wave signal) are detected, respectively. Peak detection of the electrocardiographic signal and peak detection of the photoelectric pulse wave signal (acceleration pulse wave signal) are performed within a normal range of a heartbeat interval and a normal range of a pulse interval, respectively. Note that the normal ranges of the heartbeat interval and the pulse interval used here are those having been set in step S132, which will be explained later, when the present flow of process was last executed. Further, information such as peak time, peak amplitude, and so on for all the detected peaks is stored. When a shift of peak being considered, each peak may be detected after predictive correction performed based on a correction value having been set previously, alternatively, candidate peaks may be detected first inside and beyond the normal range and determined again whether or not each of the peaks is within the normal range after a shift of each peak is corrected in step S106, which will be explained later.

In the subsequent step S106, delay times (shift amounts) of the electrocardiographic signal R-wave peak and the photoelectric pulse wave signal (acceleration pulse wave) are respectively obtained, and the electrocardiographic signal R-wave peak and the photoelectric pulse wave signal (acceleration pulse wave) peak are respectively corrected based on the above obtained delay times. Since the manner in which the delay times of the respective peaks are obtained is the same as described before, detailed description thereof is omitted herein.

Next, in step S108, it is determined whether or not peaks of a electrocardiographic signal and the photoelectric pulse wave signal (acceleration pulse wave signal) are respectively detected within the heartbeat interval normal range and the pulse interval normal range. In the case where none of the peaks thereof are detected to be within the normal ranges, determination of error is made in step S110 (that is, the heartbeat interval, pulse interval, and pulse wave propagation time are all determined to be errors). Thereafter, the process once exits from the present flow of process. On the other hand, in the case where any peaks are detected in any one or both of the electrocardiographic signal normal range and the photoelectric pulse wave signal (acceleration pulse wave signal) normal range, the process goes to step S112.

In step S112, it is determined whether or not a peak within the heartbeat interval normal range is detected in the electrocardiographic signal. If any peak is not detected within the normal range, a peak of the photo electric pulse wave (acceleration pulse wave) signal is selected in step S114. More specifically, of a plurality of peaks in the photoelectric pulse wave (acceleration pulse wave) signal, a peak of the photoelectric pulse wave (acceleration pulse wave) signal which is more likely to be accurate is selected based on peak amplitude, a change rate of the prior heartbeat intervals (intervals of immediately prior several heartbeats), or the like, for example. At this time, a change rate of the peak amplitude or the like may be added to the selection standards. Then, in step S116, only the pulse interval is outputted. Thereafter, the process goes to step S132. Meanwhile, if a peak within the normal range is detected, the process goes to step S118.

In step S118, it is determined whether or not a peak within the pulse interval normal range is detected in the photoelectric pulse wave signal (acceleration pulse wave signal). If any peak is not detected within the normal range, a peak of the electrocardiographic signal is selected in step S120. More specifically, of a plurality of peaks in the electrocardiographic signal, a peak of the electrocardiographic signal which is more likely to be accurate is selected based on peak amplitude, a change rate of the prior pulse intervals (intervals of immediately prior several pulses), or the like, for example. At this time, a change rate of the peak amplitude or the like may be added to the selection standards. Then, in step S122, only the heartbeat interval is outputted. Thereafter, the process goes to step S132. Meanwhile, if a peak within the normal range is detected, the process goes to step S124.

In step S124, peaks of the electrocardiographic signal and the photoelectric pulse wave (acceleration pulse wave) signal are respectively selected. More specifically, of the plurality of peaks in the electrocardiographic signal and the photoelectric pulse wave (acceleration pulse wave) signal, a peak of the electrocardiographic signal and a peak of the photoelectric pulse wave (acceleration pulse wave) signal which are more likely to be accurate are selected based on each peak amplitude, each change rate of the prior heartbeat and pulse intervals (intervals of immediately prior several heartbeats and pulses), or the like, for example. At this time, a change rate of each peak amplitude or the like may be added to the selection standards.

Next, in step S126, whether a pulse wave propagation time is abnormal or not is determined. If the pulse wave propagation time is abnormal, the process goes to step S128. On the other hand, if the pulse wave propagation time is not abnormal, the process goes to step S130.

In step S128, whether or not the heartbeat interval change rate is greater than the pulse interval change rate is determined. If the heartbeat interval change rate is greater than the pulse interval change rate, only the pulse wave interval is outputted in step S116. Thereafter, the process goes to step S132. On the other hand, if the heartbeat interval change rate is equal to or less than the pulse interval change rate, only the heartbeat interval is outputted in step S122. Thereafter, the process goes to step S132.

Meanwhile, in step S130, the heartbeat interval, the pulse interval, and the pulse wave propagation time are outputted to the display unit 340 or the like. Note that the obtained heartbeat interval (heart rate) and pulse interval (pulse rate) are used in the above-mentioned step S106 when the present flow of process is executed next time.

Next, in step S132, normal ranges of the heartbeat interval, pulse interval, and pulse wave propagation time are respectively set. Regarding the normal ranges of the heartbeat and pulse intervals, in addition to the typical range (for example, 0.3 seconds to 1.5 seconds), ranges in which the change rates with respect to the prior heartbeat and pulse intervals (intervals of immediately prior several heartbeats and pulses) are each equal to or less than a predetermined value are also set as the normal ranges thereof. Note that the set normal values of the heartbeat interval and pulse interval are used in the above-mentioned steps S104 and S106 when the present flow of process is executed next time. Likewise, regarding the normal range of the pulse wave propagation time, in addition to the typical range (for example, equal to or less than approximately 0.3 seconds), a range in which the change rate with respect to the prior pulse wave propagation times (propagation times for immediately prior several heartbeats and pulses) is equal to or less than a predetermined value is also set as the normal range thereof. Note that the set normal value of the pulse wave propagation time is used in the above-mentioned step S126 when the present flow of process is executed next time. Then, the present flow of process ends.

According to the present embodiment, as described thus far, performing the signal process including the filtering processing makes it possible to obtain an electrocardiographic signal and a photoelectric pulse wave signal at preferable S/N ratios. Further, since the corrections are made on the delay times of the electrocardiographic signal and the photoelectric pulse wave signal due to the signal process of the detected electrocardiographic signal peak and photoelectric pulse wave signal peak, it is possible to more accurately specify the respective peaks of the electrocardiographic signal and the photoelectric pulse wave signal. As such, the pulse wave propagation time can be more precisely measured.

Further, according to the present embodiment, a delay time of the electrocardiographic signal and a delay time of the photoelectric pulse wave signal are obtained based on the respective frequency components of the electrocardiographic signal and the photoelectric pulse wave signal. Accordingly, even if the first signal processing section 310 and the second signal processing section 320, both of which include the filters, have frequency characteristics (frequency dependency) and the amount of shift of each peak (delay time) varies depending on each of the frequency components of the electrocardiographic signal and the photoelectric pulse wave signal, each of the shifts can be appropriately corrected. This makes it possible to more precisely measure the pulse wave propagation time.

Furthermore, according to the present embodiment, the above-mentioned frequency components can be defined in accordance with the pulse rate or the heart rate. In other words, by making use of the pulse rate obtained from the photoelectric pulse wave signal or the heart rate obtained from the electrocardiographic signal, it is possible to obtain the frequency components relatively with ease without performing a special or dedicated process (for example, FFT or the like).

According to the present embodiment, in the case where a plurality of peaks of the electrocardiographic signal having different polarities are detected, a peak which forms the longest pulse wave propagation time within a predetermined time is determined to be a true peak. This makes it possible to correctly detect a peak even in a case where portions of a biological body with which the first and second electrocardiographic electrodes 11 and 12 make contact are reversed, a user has a physical constitution such that an R-wave (peak) included in an electrocardiographic signal is formed upside down, or the like. In addition, because an electrocardiographic waveform differs depending on a measurement portion, the physical constitution of a user, or the like, and deforms when experiencing filtering, R-waves are formed at both the upper and lower sides in some case; however, even in this case, the peak can be correctly detected. As such, the pulse wave propagation time can be measured more precisely.

Moreover, according to the present embodiment, in the case where an obtained pulse wave propagation time does not fall within a predetermined time, this obtained pulse wave propagation time is determined to be an error. In other words, in the case where the obtained pulse wave propagation time does not fall within the predetermined range, taking the measurement result as an error makes it possible to prevent an erroneous measurement of the pulse wave propagation time. By doing so, the precision in peak error determination of an electrocardiographic R-wave peak and a photoelectric pulse wave (acceleration pulse wave) peak can be enhanced in comparison with a case in which the determination of error is made only based on the heartbeat interval and the pulse interval.

According to the present embodiment, in the case where an obtained pulse wave propagation time does not fall within a predetermined time, the detected electrocardiographic signal peak is determined to be an error when a change rate of the heartbeat interval is larger than a change rate of the pulse interval, and the obtained photoelectric pulse wave signal peak is determined to be an error when the change rate of the pulse interval is larger than the change rate of the heartbeat interval. In other words, by specifying which of the peak of the electrocardiographic signal and the peak of the photoelectric pulse wave signal is erroneously detected, it is possible to obtain, for example, data of the pulse interval, the heartbeat interval, or the like by using the peak which is detected as being not erroneous.

Another Process Mode

In the above-described process mode, there is a high possibility that noise is erroneously detected as an electrocardiographic R-wave peak and/or a photoelectric pulse wave (acceleration pulse wave) peak in a case where an obtained pulse wave propagation time does not fall within a predetermined time; as such, it is determined that an erroneous obtainment has occurred in this case. However, of the combinations of a plurality of the peaks even including additional peaks present near the detected peaks, a combination in which a heartbeat interval, a pulse interval, and a pulse wave propagation time are each within a predetermined range and the change rates of the pulse wave propagation time and so on become smaller may be selected, and then the heartbeat interval, the pulse interval, and the pulse wave propagation time may be calculated from the peaks included in the selected combination.

Further, unlike the above case, in the case where no appropriate combination is present, the electrocardiographic R-wave peak may be determined to be noise and the heartbeat interval and the pulse wave propagation time may be taken as being erroneously obtained if the change rate of the heartbeat interval is larger than that of the pulse interval; conversely, the photoelectric pulse wave (acceleration pulse wave) peak may be determined to be noise and the pulse interval and the pulse wave propagation time may be taken as being erroneously obtained if the change rate of the heartbeat interval is smaller than that of the pulse interval.

According to the process mode described before, in the example in FIG. 7 discussed above, since an absolute value of ((heartbeat interval 2'−heartbeat interval 1)/heartbeat interval 1) is greater than an absolute value of ((pulse interval 2−pulse interval 1)/pulse interval 1), the electrocardiographic R-wave peak is determined to be noise and the heartbeat interval and the pulse wave propagation time are taken as being erroneously obtained so that only the pulse interval is obtained.

Figure 3:
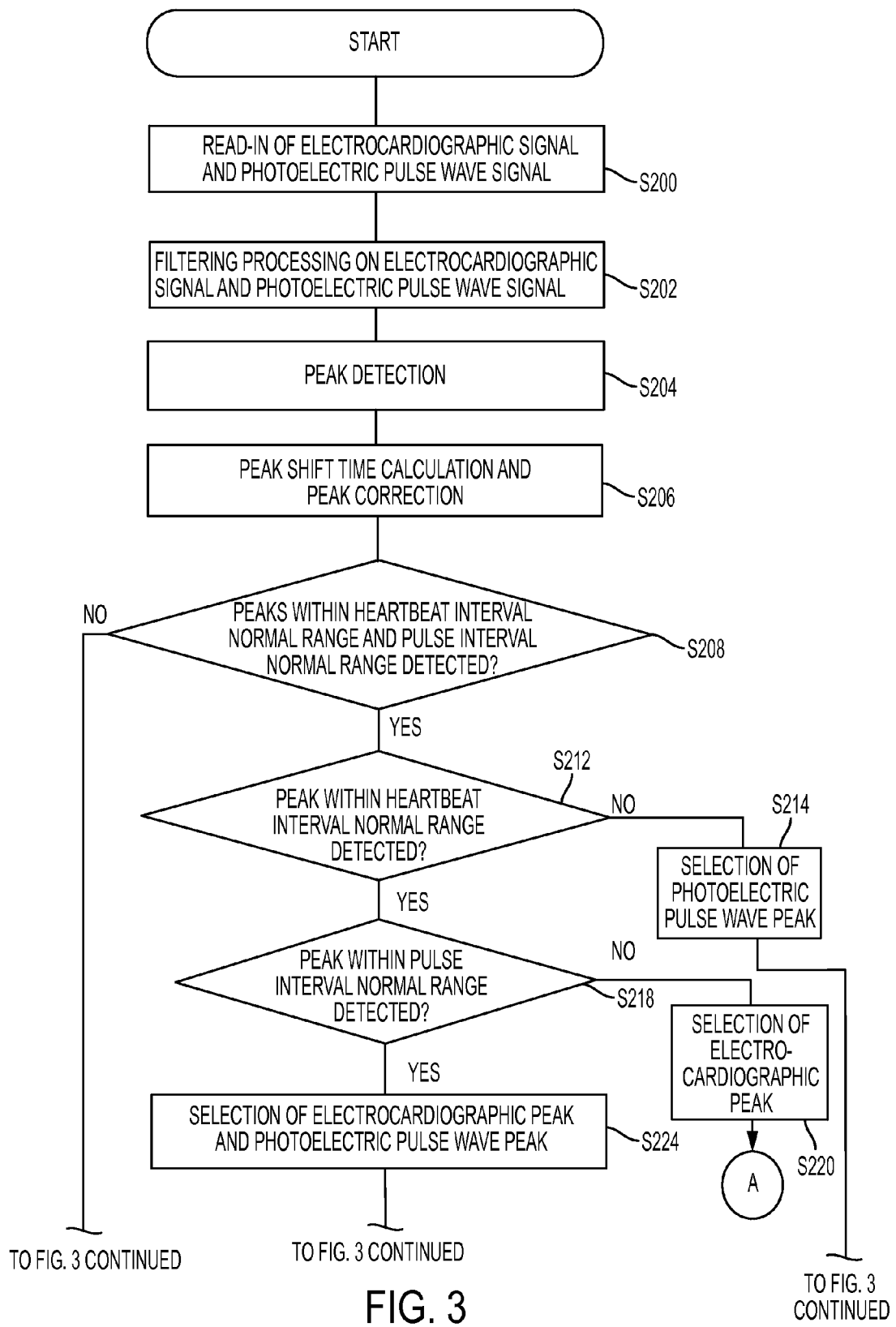
FIG. 3 is a flowchart illustrating another sequence of steps of a pulse wave propagation time measurement process carried out by a pulse wave propagation time measurement device according to an embodiment.
Figure 3:
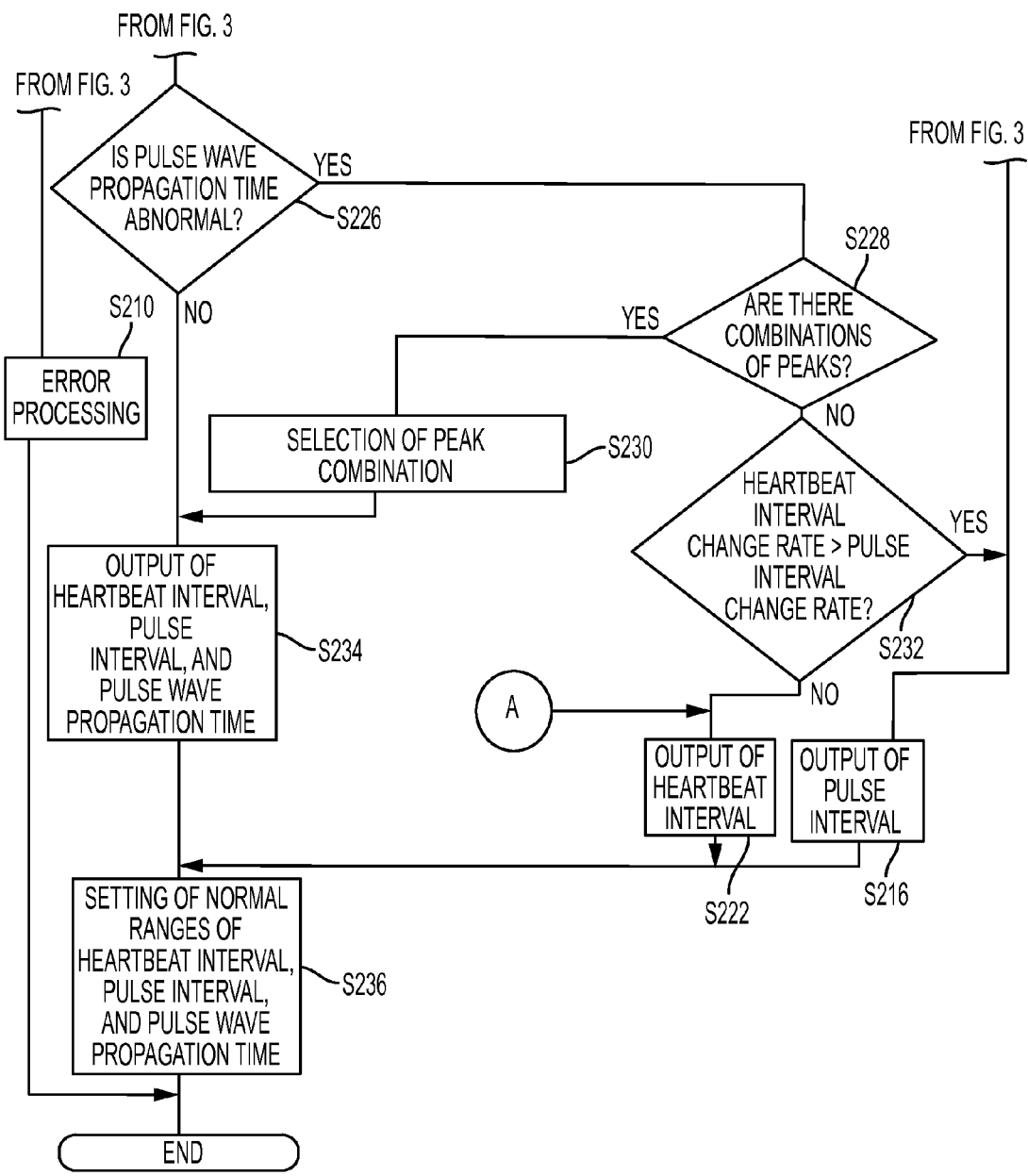

As such, another sequence of steps (another process mode) of a pulse wave propagation time measurement process will be described next with reference to FIG. 3. Here, FIG. 3 is a flowchart illustrating another sequence of steps of a pulse wave propagation time measurement process carried out by the pulse wave propagation time measurement device 1.

In step S200, an electrocardiographic signal (electrocardiographic waveform) detected by the electrocardiographic sensor 10 and a photoelectric pulse wave signal (photoelectric pulse waveform) detected by the photoelectric pulse wave sensor 20 are read in. In the subsequent step S202, filtering processing is performed on the electrocardiographic signal (electrocardiographic waveform) and the photoelectric pulse wave signal (photoelectric pulse waveform) having been read in in step S200. Further, an acceleration pulse wave is obtained through performing second order differential on the photoelectric pulse wave signal.

Next, in step S204, peaks of the electrocardiographic signal and the photoelectric pulse wave signal (acceleration pulse wave signal) are detected, respectively. Peak detection of the electrocardiographic signal and peak detection of the photoelectric pulse wave signal (acceleration pulse wave signal) are performed within a normal range of a heartbeat interval and a normal range of a pulse interval, respectively. Note that the normal ranges of the heartbeat interval and the pulse interval used here are those having been set in step S236, which will be explained later, when the present flow of process was last executed. Further, information such as peak time, peak amplitude, and so on for all the detected peaks is stored. When a shift of peak being considered, each peak may be detected after predictive correction performed based on a correction value having been set previously, alternatively, candidate peaks may be detected first inside and beyond the normal range and determined again whether or not each of the peaks is within the normal range after a shift of each peak is corrected in step S206, which will be explained later.

In the subsequent step S206, delay times (shift amounts) of the electrocardiographic signal R-wave peak and the photoelectric pulse wave signal (acceleration pulse wave) are respectively obtained, and the electrocardiographic signal R-wave peak and the photoelectric pulse wave signal (acceleration pulse wave) peak are respectively corrected based on the above obtained delay times. Since the method in which the delay times of the respective peaks are obtained is the same as described before, detailed description thereof is omitted herein.

Next, in step S208, it is determined whether or not peaks of the electrocardiographic signal and the photoelectric pulse wave signal (acceleration pulse wave signal) are respectively detected within the heartbeat interval normal range and the pulse interval normal range. In the case where none of the peaks thereof are detected to be within the normal ranges, determination of error is made in step S210 (that is, the heartbeat interval, pulse interval, and pulse wave propagation time are all determined to be errors). Thereafter, the process once exits from the present flow of process. On the other hand, in the case where any peaks are detected in any one or both of the electrocardiographic signal normal range and the photoelectric pulse wave signal (acceleration pulse wave signal) normal range, the process goes to step S212.

In step S212, it is determined whether or not a peak within the heartbeat interval normal range is detected in the electrocardiographic signal. If any peak is not detected within the normal range, a peak of the photo electric pulse wave (acceleration pulse wave) signal is selected in step S214. More specifically, of a plurality of peaks in the photoelectric pulse wave (acceleration pulse wave) signal, a peak of the photoelectric pulse wave (acceleration pulse wave) signal which is more likely to be accurate is selected based on peak amplitude, a change rate of the prior heartbeat intervals (intervals of immediately prior several heartbeats), or the like, for example. At this time, a change rate of the peak amplitude or the like may be added to the selection standards. Then, in step S216, only the pulse interval is outputted. Thereafter, the process goes to step S236. Meanwhile, if a peak within the normal range is detected, the process goes to step S218.

In step 218, it is determined whether or not a peak within the pulse interval normal range is detected in the photoelectric pulse wave signal (acceleration pulse wave signal). If any peak is not detected within the normal range, a peak of the electrocardiographic signal is selected in step S220. More specifically, of a plurality of peaks in the electrocardiographic signal, a peak of the electrocardiographic signal which is more likely to be accurate is selected based on peak amplitude, a change rate of the prior pulse intervals (intervals of immediately prior several pulses), for example. At this time, a change rate of the peak amplitude or the like may be added to the selection standards. Then, in step S222, only the heartbeat interval is outputted. Thereafter, the process goes to step S236. Meanwhile, if a peak within the normal range is detected, the process goes to step S224.

In step S224, peaks of the electrocardiographic signal and the photoelectric pulse wave (acceleration pulse wave) signal are respectively selected. More specifically, of the plurality of peaks in the electrocardiographic signal and the photoelectric pulse wave (acceleration pulse wave) signal, a peak of the electrocardiographic signal and a peak of the photoelectric pulse wave (acceleration pulse wave) signal which are more likely to be accurate are selected based on each peak amplitude, each change rate of the prior heartbeat and pulse intervals (intervals of immediately prior several heartbeats and pulses), or the like, for example. At this time, a change rate of each peak amplitude or the like may be added to the selection standards.

Next, in step S226, whether a pulse wave propagation time is abnormal or not is determined. If the pulse wave propagation time is abnormal, the process goes to step S228. On the other hand, if the pulse wave propagation time is not abnormal, the process goes to step S234.

In step S228, it is determined whether or not there exists a combination of peaks, among the combinations of one or more detected electrocardiographic signal peaks and one or more detected photoelectric pulse wave signal peaks, that allows a pulse wave propagation time to be within a predetermined range. If there exists such peak combination, the process goes to S230. On the other hand, if such peak combination does not exist, the process goes to step S232.

In step S230, a combination of peaks is selected. More specifically, selection of a combination of peaks is made in step S230 while considering at least one of the change rate of the pulse wave propagation time, the peak amplitude of the electrocardiographic signal and the change rate of the stated amplitude, the peak amplitude of the photoelectric pulse wave signal and the change rate of the stated amplitude, the change rate of the heartbeat interval, and the change rate of the pulse interval, so as to obtain the pulse wave propagation time. Thereafter, the process goes to step S234.

In step S232, whether or not the heartbeat interval change rate is greater than the pulse interval change rate is determined. If the heartbeat interval change rate is greater than the pulse interval change rate, only the pulse wave interval is outputted in step S216. Thereafter, the process goes to step S236. On the other hand, if the heartbeat interval change rate is equal to or less than the pulse interval change rate, only the heartbeat interval is outputted in step S222. Thereafter, the process goes to step S236.

Meanwhile, in step S234, the heartbeat interval, the pulse interval, and the pulse wave propagation time are outputted to the display unit 340 or the like. Note that the obtained heartbeat interval (heart rate) and pulse interval (pulse rate) are used in the above-mentioned step S206 when the present flow of process is executed next time.

Next, in step S236, normal ranges of the heartbeat interval, pulse interval, and pulse wave propagation time are respectively set. Regarding the normal ranges of the heartbeat and pulse intervals, in addition to the typical range (for example, 0.3 seconds to 1.5 seconds), ranges in which the change rates with respect to the prior heartbeat and pulse intervals (intervals of immediately prior several heartbeats and pulses) are each equal to or less than a predetermined value are also set as the normal ranges thereof. Note that the set normal values of the heartbeat interval and pulse interval are used in the above-mentioned steps S204 and S206 when the present flow of process is executed next time. Likewise, regarding the normal range of the pulse wave propagation time, in addition to the typical range (for example, equal to or less than approximately 0.3 seconds), a range in which the change rate with respect to the prior pulse wave propagation times (propagation times for immediately prior several heartbeats and pulses) is equal to or less than a predetermined value is also set as the normal range thereof. Note that the set normal value of the pulse wave propagation time is used in the above-mentioned step S226 when the present flow of process is executed next time. Then, the present flow of process ends.

According to the present process mode, even in a case where a pulse wave propagation time measurement value does not fall within a predetermine time, a pulse wave propagation time which is more likely to be accurate can be obtained.

Thus far, the embodiments of the present invention have been discussed. Note that, however, the present invention is not intended to be limited to the above embodiments, and various modifications can be made thereupon. For example, although polarities of electrocardiographic wave peaks are automatically determined in the above embodiment, the configuration may be such that an inverter 315 (inverting means) to invert the polarities of electrocardiographic signals is provided between the digital filter 314 and the peak detector 316 as shown in FIG. 1 where the inverter 315 is illustrated with a broken line with a rectangular frame. Alternatively, a configuration in which a user physically switches interconnections provided between the first and second electrocardiographic electrodes 11, 12 and the amplifying section 311 may be employed.

In the case where the inverter 315 is provided, the inverter 315 inverts the polarity of an electrocardiographic signal when the pulse wave propagation time measurement section 330 determines that an R-wave peak of the electrocardiographic signal is formed at the lower side of the signal. That is, the electrocardiographic wave is converted upside down. Through this, even in a case where portions of a biological body with which the first and second electrocardiographic electrodes 11 and 12 make contact are reversed, the physical constitution of a user is such that an R-wave (peak) included in an electrocardiographic signal is formed upside down, or the like, inverting the polarity of the electrocardiographic signal makes it possible to correctly detect the peak and measure a pulse wave propagation time with precision.

Although a pulse rate is used when obtaining the frequency components of an electrocardiographic signal and a photoelectric pulse wave signal in the above embodiment, the configuration may be such that the frequency components are obtained by performing processing such as FFT or the like.

Further, in the embodiment, a delay time (amount of shift) of each peak is obtained based on the frequency components of the electrocardiographic signal and the photoelectric signal. However, in the case where the analog filters 312, 322 and the digital filter 314, 324 are so designed that the frequency characteristics thereof do not largely vary within a frequency range of the pulsation component, a configuration in which the delay time (amount of shift) of the peak can be assumed to be substantially constant so as to calculate a pulse wave propagation time may be employed.

REFERENCE SIGNS LIST 1 pulse wave propagation time measurement device
10 electrocardiographic sensor
11 first electrocardiographic electrode
12 second electrocardiographic electrode
20 photoelectric pulse wave sensor
21 light-emitting element
22 light-receiving element
30 signal processing unit
310 first signal processing section
320 second signal processing section
311, 321 amplifying section
312, 322 analog filter
313, 323 A/D converter
341, 324 digital filter
315 inverter
325 second order differential processor
316, 326 peak detector
317, 327 delay time obtaining section
318, 328 peak corrector
330 pulse wave propagation time measurement section
340 display unit
350 driver

The invention claimed is:

1. A pulse wave propagation time measurement device comprising:
    an electrocardiographic sensor including at least one electrocardiographic electrode configured to detect an electrocardiographic signal;
    a photoelectric pulse wave sensor including a light-emitting element and a light-receiving element configured to detect a photoelectric pulse wave signal;
    a first signal processor configured to filter the electrocardiographic signal;
    a second signal processor configured to filter the photoelectric pulse wave signal;
    a peak detector configured to detect a peak of the electrocardiographic signal filtered by the first signal processor and a peak of the photoelectric pulse wave signal filtered by the second signal processor;
    a delay time obtaining unit configured to obtain a delay time of at least one of the electrocardiographic signal filtered by the first signal processor and the photoelectric pulse wave signal filtered by the second signal processor;
    a correcting unit configured to correct at least one of the peak of the electrocardiographic signal and the peak of the photoelectric pulse wave signal detected by the peak detector based on at least one of the delay time of the electrocardiographic signal and the photoelectric pulse wave signal obtained by the delay time obtaining unit; and
    a calculating unit configured to calculate a pulse wave propagation time from a time difference between the peak of the photoelectric pulse wave signal and the peak of the electrocardiographic signal corrected by the correcting unit.

2. The pulse wave propagation time measurement device according to claim 1, wherein the delay time obtaining unit is configured to obtain the delay time of the electrocardiographic signal and the photoelectric pulse wave signal based on frequency components of the electrocardiographic signal and the photoelectric pulse wave signal, respectively.

3. The pulse wave propagation time measurement device according to claim 2, wherein the frequency components correspond to a pulse rate obtained from the photoelectric pulse wave signal or a heart rate obtained from the electrocardiographic signal.

4. The pulse wave propagation time measurement device according to claim 1, further comprising an inverting circuit configured to invert polarity of the electrocardiographic signal detected by the electrocardiographic sensor.

5. The pulse wave propagation time measurement device according to claim 1, wherein, when a plurality of peaks of the electrocardiographic signal have different polarities, the calculating unit calculates a peak that forms a longest pulse wave propagation time within a predetermined time as a true peak among the plurality of peaks of the electrocardiographic signal.

6. The pulse wave propagation time measurement device according to claim 1, wherein the calculating unit determines that the calculated pulse wave propagation time is in error when the calculated pulse wave propagation time is not within a predetermined time.

7. The pulse wave propagation time measurement device according to claim 1, wherein, when the calculated pulse wave propagation time is not within a predetermined time, the calculating unit determines the detected peak of the electrocardiographic signal is in error when a change rate of a heartbeat interval is larger than a change rate of a pulse interval.

8. The pulse wave propagation time measurement device according to claim 1, wherein, when the calculated pulse wave propagation time is not within a predetermined time, the calculating unit determines the detected peak of the photoelectric pulse wave signal is in error when a change rate of the pulse interval is larger than a change rate of the heartbeat interval.

9. The pulse wave propagation time measurement device according to claim 1, wherein, when the calculated pulse wave propagation time is not within a predetermined time, the calculating unit:

searches for a combination of an electrocardiographic signal peak and a photoelectric pulse wave signal peak from the detected peak and one or more additional peaks of the electrocardiographic signal, and the detected peak and one or more additional peaks of the photoelectric pulse wave signal peaks that allows a pulse wave propagation time to fall within the predetermined time, selects the combination based on at least one of a rate of change of the pulse wave propagation time, amplitude of the electrocardiographic signal peak and rate of change of the amplitude, amplitude of the photoelectric pulse wave signal peak and a rate of change of the amplitude, a rate of change rate of the heartbeat interval, and a rate of change rate of the pulse interval; and calculates the pulse wave propagation time based on the selecting combination.

10. A method for determining a pulse wave propagation time, the method comprising:
   detecting, by an electrocardiographic sensor, an electrocardiographic signal;
   detecting, by a photoelectric pulse wave sensor, a photoelectric pulse wave signal;
   filtering by at least one signal processor, the electrocardiographic signal and the photoelectric pulse wave signal;
   detecting a peak of the electrocardiographic signal and a peak of the photoelectric pulse wave signal;
   obtaining a delay time of at least one of the electrocardiographic signal and the photoelectric pulse wave signal;
   correcting at least one of the peak of the electrocardiographic signal and the peak of photoelectric pulse wave signal based on at least one of the delay time of the electrocardiographic signal and the delay time of the photoelectric pulse wave signal, respectively; and
   calculating a pulse wave propagation time from a time difference between the peak of the photoelectric pulse wave signal and the peak of the electrocardiographic signal.

11. The method of determining pulse wave propagation time according to claim 10, further comprising obtaining the delay time of the electrocardiographic signal and the delay time of the photoelectric pulse wave signal based on frequency components of the electrocardiographic signal and the photoelectric pulse wave signal, respectively.

12. The method of determining pulse wave propagation time according to claim 11, wherein the frequency components correspond to a pulse rate obtained from the photoelectric pulse wave signal or a heart rate obtained from the electrocardiographic signal.

13. The method of determining pulse wave propagation time according to claim 10, further comprising inverting a polarity of the detected electrocardiographic signal.

14. The method of determining pulse wave propagation time according to claim 10, further comprising calculating a peak that forms a longest pulse wave propagation time within a predetermined time as a true peak among a plurality of peaks of the electrocardiographic signal when the plurality of peaks of the electrocardiographic signal have different polarities.

15. The method of determining pulse wave propagation time according to claim 10, further comprising determining that the calculated pulse wave propagation time is in error when the calculated pulse wave propagation time is not within a predetermined time.

16. The method of determining pulse wave propagation time according to claim 10, wherein, when the calculated pulse wave propagation time is not within a predetermined time, the method further comprises determining the detected peak of the electrocardiographic signal is in error when a change rate of a heartbeat interval is larger than a change rate of a pulse interval.

17. The method of determining pulse wave propagation time according to claim 10, wherein, when the calculated pulse wave propagation time is not within a predetermined time, the method further comprises determining the detected peak of the photoelectric pulse wave signal is in error when a change rate of the pulse interval is larger than a change rate of the heartbeat interval.

18. The method of determining pulse wave propagation time according to claim 10, wherein, when the calculated pulse wave propagation time is not within a predetermined time, the method further comprises:
   searching for a combination of an electrocardiographic signal peak and a photoelectric pulse wave signal peak from the detected peak and one or more additional peaks of the electrocardiographic signal, and the detected peak and one or more additional peaks of the photoelectric pulse wave signal peaks that allows a pulse wave propagation time to fall within the predetermined time,
   selecting the combination based on at least one of a rate of change of the pulse wave propagation time, amplitude of the electrocardiographic signal peak and rate of change of the amplitude, amplitude of the photoelectric pulse wave signal peak and a rate of change of the amplitude, a rate of change rate of the heartbeat interval, and a rate of change rate of the pulse interval; and
   calculating the pulse wave propagation time based on the selecting combination.

19. A pulse wave propagation time measurement device comprising:
   an electrocardiographic sensor including at least one electrocardiographic electrode configured to detect an electrocardiographic signal;
   a photoelectric pulse wave sensor including a light-emitting element and a light-receiving element configured to detect a photoelectric pulse wave signal;
   a plurality of filters configured to filter the electrocardiographic signal and the photoelectric pulse wave signal, respectively; and
   at least one hardware processor configured to:
      detect a peak of the electrocardiographic signal filtered by the first signal processor and a peak of the photoelectric pulse wave signal filtered by the second signal processor,
      obtain a delay time of at least one of the electrocardiographic signal filtered by the first signal processor and the photoelectric pulse wave signal filtered by the second signal processor,
      correct at least one of the peak of the electrocardiographic signal and the peak of the photoelectric pulse wave signal detected by the peak detector based on at least one of the delay time of the electrocardiographic signal and the delay time of the photoelectric pulse wave signal, and
      calculate a pulse wave propagation time from a time difference between the peak of the photoelectric pulse wave signal and the peak of the electrocardiographic signal corrected by the correcting unit.

20. The pulse wave propagation time measurement device according to claim 19, wherein, when the calculated pulse wave propagation time is not within a predetermined time, the at least one hardware processor is further configured to determines the detected peak of the electrocardiographic signal is in error when:
  a change rate of a heartbeat interval is larger than a change rate of a pulse interval, or
  a change rate of the pulse interval is larger than a change rate of the heartbeat interval.

* * * * *